(12) United States Patent
Riordan et al.

(10) Patent No.: US 10,386,324 B2
(45) Date of Patent: Aug. 20, 2019

(54) SUSCEPTANCE MEASUREMENT FOR IDENTIFYING BIOCHEMICAL SENSORS

(71) Applicant: Analog Devices Global, Hamilton (BM)

(72) Inventors: Liam Riordan, Raheen (IE); Tudor M Vinereanu, Cork (IE); Paul V. Errico, Andover, MA (US); Dermot G. O'Keeffe, Blarney (IE); Camille L. Huin, Taipei (TW); Donal Bourke, Mallow (IE)

(73) Assignee: Analog Devices Global, Hamilton (BM)

( * ) Notice: Subject to any disclaimer, the term of this patent is extended or adjusted under 35 U.S.C. 154(b) by 632 days.

(21) Appl. No.: 15/050,141

(22) Filed: Feb. 22, 2016

(65) Prior Publication Data

US 2017/0241939 A1   Aug. 24, 2017

(51) Int. Cl.
  *G01N 27/327*   (2006.01)
  *G06K 9/62*   (2006.01)
  *C12Q 1/00*   (2006.01)
  *G06K 9/52*   (2006.01)
  *G01N 33/487*   (2006.01)

(52) U.S. Cl.
  CPC ......... *G01N 27/3274* (2013.01); *C12Q 1/001* (2013.01); *G01N 27/327* (2013.01); *G01N 27/3272* (2013.01); *G01N 27/3273* (2013.01); *G06K 9/522* (2013.01); *G06K 9/6212* (2013.01); *G01N 33/48771* (2013.01)

(58) Field of Classification Search
  CPC ........... G01N 27/3273; G01N 27/3274; G01N 33/48771; Y10T 29/49004
  See application file for complete search history.

(56) References Cited

U.S. PATENT DOCUMENTS 7,645,373 B2   1/2010   Groll et al.
8,206,565 B2   6/2012   Grool et al.
(Continued)

FOREIGN PATENT DOCUMENTS

WO   WO-2017144456 A1   8/2017

OTHER PUBLICATIONS

"International Application Serial No. PCT/EP2017/053920, International Search Report dated Jun. 20, 2017", 4 pgs.
(Continued)

*Primary Examiner* — Gurpreet Kaur (74) *Attorney, Agent, or Firm* — Schwegman Lundberg & Woessner, P.A.

(57) ABSTRACT

Subject matter herein can include identifying a biochemical test strip assembly electrically, such as using the same test circuitry as can be used to perform an electrochemical measurement, without requiring use of optical techniques. The identification can include using information about a measured susceptance of an identification feature included as a portion of the test strip assembly. The identification can be used by test circuitry to select test parameters or calibration values, or to select an appropriate test protocol for the type of test strip coupled to the test circuitry. The identification can be used by the test circuitry to validate or reject a test strip assembly, such as to inhibit use of test strips that fail meet one or more specified criteria.

22 Claims, 7 Drawing Sheets

(56) References Cited

U.S. PATENT DOCUMENTS

| | | |
|---|---|---|
| 2008/0237040 A1 | 10/2008 | Wessel |
| 2009/0078588 A1 | 3/2009 | Lin et al. |
| 2012/0262298 A1* | 10/2012 | Bohm ................ G01N 27/3274 340/604 |
| 2014/0246322 A1* | 9/2014 | Katsumoto ............ B03C 5/005 204/643 |
| 2015/0136617 A1* | 5/2015 | Cheng ................ G01N 27/3274 205/792 |
| 2015/0136853 A1 | 5/2015 | Palmer et al. |
| 2015/0178610 A1 | 6/2015 | Han et al. |

OTHER PUBLICATIONS

"International Application Serial No. PCT/EP2017/053920, Written Opinion dated Jun. 20, 2017", 8 pgs.

Kamat, D. K., et al., "Blood Glucose Measurement Using Bioimpedance Technique", *Advances in Electronics*, vol. 2014, Article ID 406257. (2014), 1-5.

"16-Bit Precision, Low Power Meter on a Chip with Cortex-M3 and Conectivity", Analog Devices—Data Sheet, (Apr. 30, 2014), 1-40.

Alva, Shridhara, "FreeStyle Lite—A Blood Glucose Meter That Requies No Coding", Journal of Diabetes Science and Technology, vol. 2, Issue 4, (Jul. 2008), 546-551.

\* cited by examiner

SUSCEPTANCE MEASUREMENT FOR IDENTIFYING BIOCHEMICAL SENSORS

TECHNICAL FIELD

This document pertains generally, but not by way of limitation, to apparatus and techniques for identifying a biochemical test strip assembly electrically.

BACKGROUND

Electrochemical measurement techniques can be used for a variety of tasks ranging from medical diagnostic tests to materials characterization, for example. In certain applications, one or more electrochemical measurements can be used to provide biochemical analysis of a sample such as to provide diagnostic information to a patient or caregiver such as a physician. In particular, parameters indicative of constituents of blood can be monitored using electrochemical measurement techniques, such as using an appropriate enzyme. Information indicative of blood parameters can then be used for other purposes such as adjustment of medication or more generalized health monitoring. In one approach, a small sample of blood from a test subject can be analyzed using a disposable test strip assembly having a sample region containing an enzyme or other reagent, and a level of a physiologic parameter can be determined using an electrical measurement. The test strip assembly can be compact and disposable, such as having electrodes to electrically couple the sample region to other test circuitry through a hardware interface. The test circuitry can include an interrogation device having a display, one or more user inputs such as buttons or soft-keys, and a hardware interface to mechanically retain the test strip and electrically couple the test strip to other circuitry included in the interrogation device. Test strip assemblies can also be used in other applications to provide compact electrochemical measurement for biochemical analysis such as for water quality monitoring, detection of noxious or toxic substances, or process monitoring.

OVERVIEW

An electrochemical measurement system can include use of a compact test strip assembly comprising a sample region, one or more reagents, measurement electrodes configured for performing an electrochemical measurement, and an electrical interface to other test circuitry. The test strip can be disposable. In one approach, optically-detectable indicia such as a bar code, or features such as apertures (e.g., holes) can be used to provide an identification of a test strip that can be decoded by another device. However, such an optical detection approach can have disadvantages. For example, to keep the test strip assembly and other circuitry compact, the addition of optical sensing circuitry can add unwanted bulk and cost to the system. An optically-scanned feature can also consume valuable exterior area of the test strip assembly, such as reducing area available for other functions or increasing the size of the test strip assembly in an unwanted manner.

The present inventors have recognized, among other things, that a test strip assembly can be automatically identified electrically, such as using the same test circuitry as can be used to perform an electrochemical measurement, without requiring use of optical techniques. Such identification or "decoding" using an electrical technique can include electrically determining an identification that is one or more of: particularized to a single test strip (a unique identification such as a corresponding to a serial number); a lot identification; a part or assembly number; or a type of test strip (e.g., to differentiate between test strips configured for different assays, such as a hormonal assay), as illustrative examples.

The identification can be used by the test circuitry such as to select test parameters or calibration values, or to select an appropriate test protocol for the type of test strip coupled to the test circuitry. In an example, the identification can be used by the test circuitry to validate or reject a test strip assembly, such as to inhibit use of test strips that fail meet one or more specified criteria (e.g., inhibiting use of a test strip from an incorrect vendor, having an incorrect lot, having an incorrect type, having an unauthorized assay for a particular patient, or having expired where testing is attempted beyond a specified expiration date).

A measured susceptance (e.g., an imaginary-valued component of the electrical admittance) of an electrical structure can provide information used for electrical identification of a test strip. In an example, an electronic system can include an excitation source configured to generate a time-varying excitation signal to be conductively coupled to a biochemical test strip assembly, and a measurement circuit comprising an analog-to-digital converter. The measurement circuit can be configured to digitize a signal elicited from the biochemical test strip assembly by the excitation signal. The measurement circuit can be configured to perform a discrete Fourier transform on the digitized signal and determine a susceptance value from the digitized signal to identify the biochemical test strip.

In an example, a technique such as a method for identifying a biochemical test strip assembly can include generating a time-varying excitation signal and conductively coupling the generated time-varying excitation signal to a biochemical test strip assembly, digitizing a signal elicited from the biochemical test strip assembly by the excitation signal, performing a discrete Fourier transform on the digitized signal, and using an output of the discrete Fourier transform, determining a susceptance value from the digitized signal to identify the biochemical test strip.

Generally, the biochemical test strip assembly includes two or more conductive regions configured to establish a specified susceptance value within a specified range when measured at a specified frequency, for measurement by the measurement circuit, the susceptance value established to permit identification the biochemical test strip assembly. A biochemical test strip assembly can include at least two measurement electrodes conductively coupled to a sample region. The biochemical test strip can include an identification feature comprising a first conductive region defining a first portion of an electrical structure and a second conductive region, conductively isolated from the first conductive region, defining a second portion of the electrical structure. The biochemical test strip can include an interface region comprising conductive portions forming an electrical interface electrically connecting the at least two measurement electrodes and the conductive portions of the identification feature of the biochemical test strip assembly to an interrogation device, where the first and second conductive regions are sized and shaped to provide a specified susceptance value within a specified range when measured at a specified frequency, the susceptance value established to permit identification the biochemical test strip assembly.

This overview is intended to provide an overview of subject matter of the present patent application. It is not intended to provide an exclusive or exhaustive explanation of the invention. The detailed description is included to provide further information about the present patent application.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
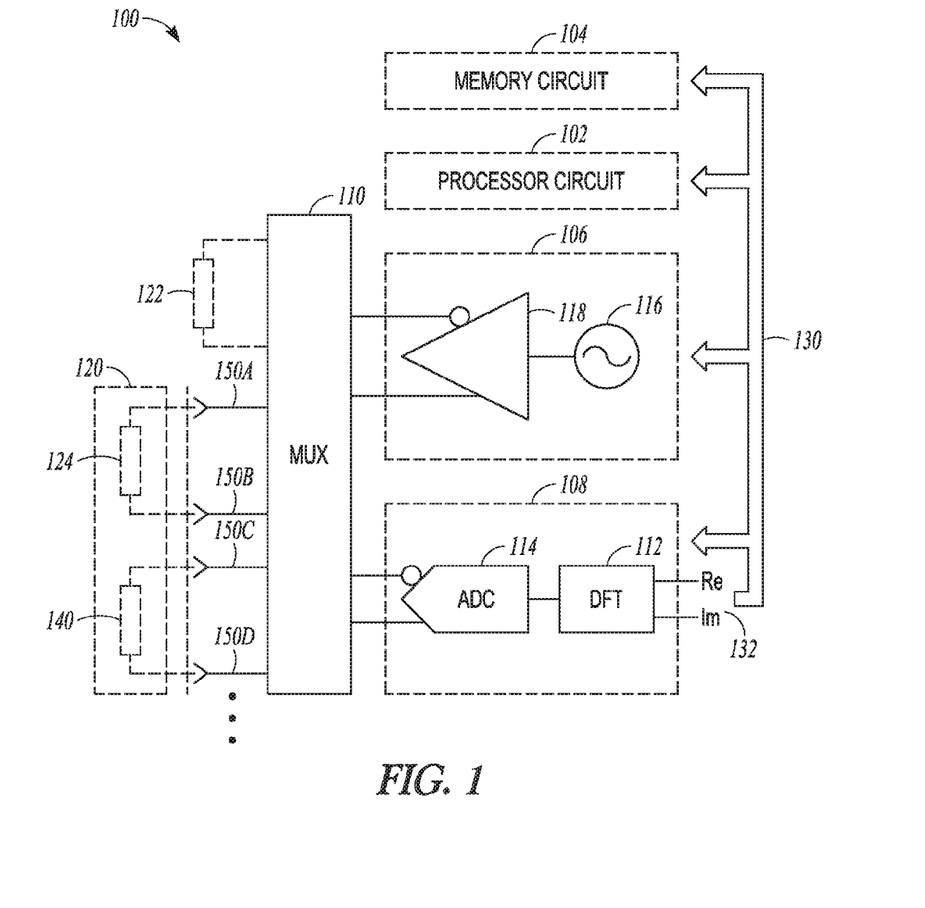
FIG. 1 illustrates generally an example comprising a system, such as can include an excitation circuit and a measurement circuit coupleable to a biochemical test strip.

FIG. 1 illustrates generally an example comprising a system 100, such as can include an excitation circuit 106 and a measurement circuit 108 coupleable to a biochemical test strip 120. The excitation circuit 106 can include an analog or discrete-time (e.g., digitally-defined or digitally-implemented) time-varying signal source 116. The signal source 116 can be coupled to one or more amplifier circuits such as an amplifier circuit 118. The amplifier 118 circuit can be configured to provide one or more of a time-varying voltage or time-varying current having a specified waveform corresponding to the signal provided by the signal source 116, and can be configured to provide single ended or differential mode output. The amplifier circuit 118 can also provide a specified direct-current (non-time-varying) bias signal either differentially or as a common-mode voltage applied to both nodes in a differential pair. As shown illustratively in FIG. 2, one or more feedback nodes can be provided by the excitation source, such as to provide flexibility in configuration of excitation amplification. Returning to FIG. 1, one or more outputs of the amplifier circuit 118 can be coupled to the biochemical test strip 120, such as through a hardware interface including terminals such as terminals 150A, 150B, 150C, or 150D. A switching circuit such as a multiplexer 110 can be provided, such as to selectively couple one or more of the terminals 150A, 150B, 150C, or 150D to the excitation circuit 106 according to a test strip identification or electrochemical measurement protocol.

The measurement circuit 108 can include an analog-to-digital converter (ADC) circuit 114, such as to digitize a signal elicited from the biochemical test strip assembly in response to an excitation signal provided by the excitation circuit 106. The measurement circuit 108 can include a discrete Fourier transform (DFT) circuit, such as a hardware-accelerated DFT circuit providing information including one or more of imaginary-valued (Im) or real-valued (Re) outputs corresponding to a real-valued or imaginary-valued component of the digitized signal at a specified measurement frequency (or a series of values across a specified range of frequencies). The present inventors have recognized, among other things, that use of a hardware-accelerated DFT circuit can rapidly and efficiently (from a power consumption standpoint) provide information indicative of an imaginary component of a digitized signal, such as can be used to determine a susceptance value of an identification feature 140 included as a portion of the biochemical test strip assembly 120.

The measurement circuit 108 can also be connected to a switching circuit or multiplexer 110 such as to provide flexibility in establishing a measurement configuration for use in identification of a biochemical test strip 120 or performing an electrochemical measurement. An electrochemical measurement (e.g., chronoamperometry) can be performed using the same excitation circuit 106 and measurement circuit 108 as are used for identification of the biochemical test strip, such as to probe a sample region 124 of the biochemical test strip. One or more of a test strip identification or electrochemical measurement protocol can be performed under the control of a processor circuit 102 such as a microcontroller or microprocessor, such as according to instructions stored in a memory circuit 104, and using a communication link 130 such as a bus or communication other interface (e.g., a low power serial interface).

For example, one or more of the excitation circuit 106, the measurement circuit 108, the processor circuit 102, and the memory circuit 104 can be co-integrated in a commonly shared integrated circuit package or module. In another example, the measurement circuit 108 and excitation circuit 106 can be co-integrated in a commonly shared integrated circuit package or module, such as including logic (e.g., a state machine, or other logic) such as can perform an excitation and measurement sequence according to a specified protocol, such as cycling through a series of control parameters stored in a table or registers according to a specified sequence. The specified sequence can be established by a separate processor circuit 102 or can be stored and performed without requiring a separate processor circuit 102.

A calibration device 122, such as a calibration resistor, can be included to facilitate calibration of the excitation circuit 106 or the measurement circuit 108. The calibration device can be included as a portion of an interrogation device assembly comprising an interrogation circuit including the excitation circuit 106 and measurement circuit 108, or the calibration device could be included as a portion of the biochemical test strip 120, or a separate "dummy" test strip used for calibration, according to various examples.

Figure 2:
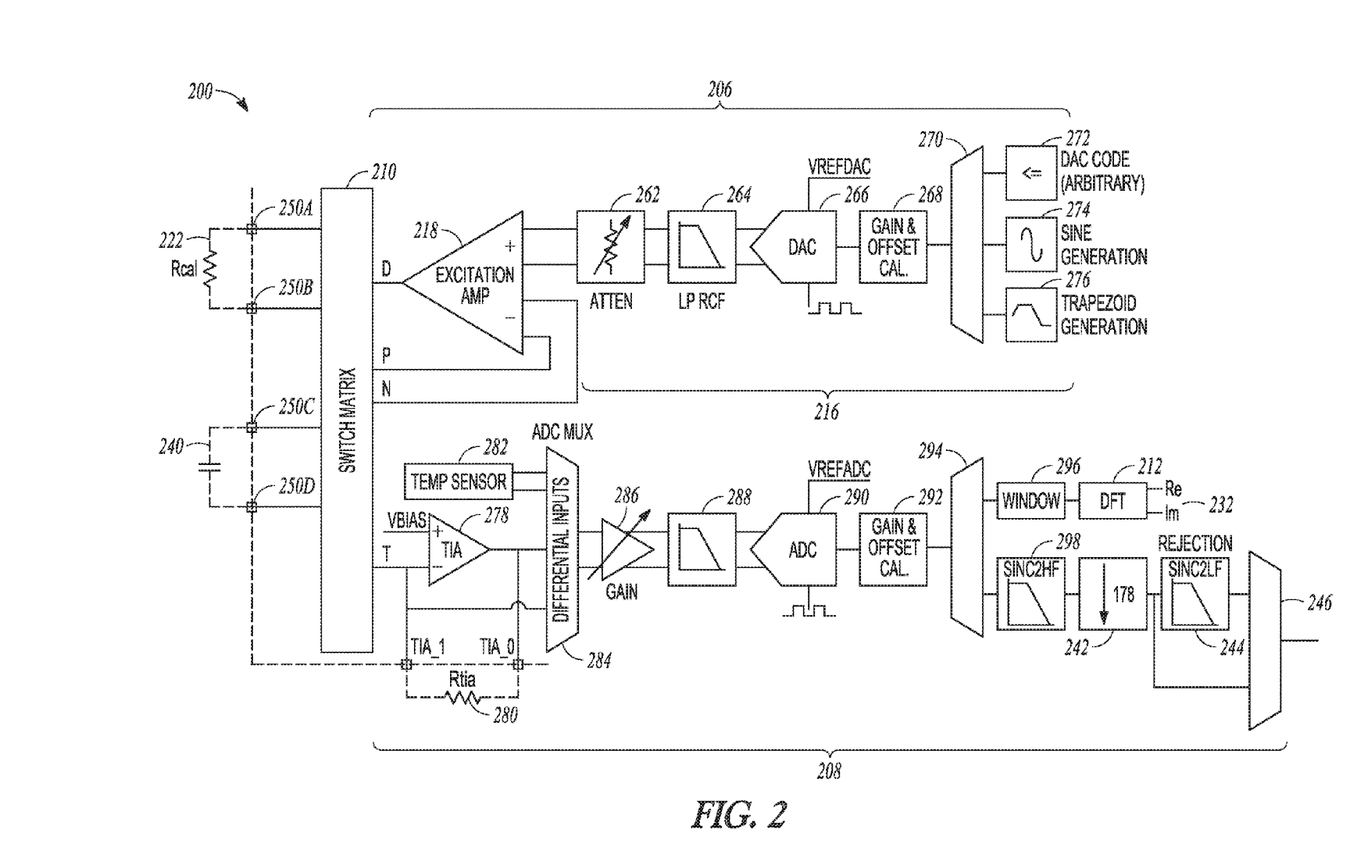
FIG. 2 illustrates generally an illustrative example of an interrogation circuit, such as can be used to perform one or more techniques recited elsewhere herein for electrical identification of a biochemical test strip.

FIG. 2 illustrates generally an illustrative example of an interrogation circuit 200, such as can be used to perform one or more techniques recited elsewhere herein for electrical identification of a biochemical test strip. In the illustrative example of FIG. 2, an excitation circuit 206 can include a signal chain having one or more signal sources such as can include an arbitrary waveform source 272 generated from a table of discrete-time values (e.g., "DAC codes"), a sine-wave generation source 274, or a trapezoid generation source 276 as illustrative examples. A multiplexer 270 can be used to select a signal source. One or more of gain or offset calibration can be applied at block 268, and a digital-to-analog converter (DAC) 266 can convert a discrete-time representation of the excitation signal to an analog signal.

A filter circuit 264 can provide a low-pass response and an attenuator 262 can be used to select a signal level in the analog domain to avoid sacrificing conversion precision. An output of the attenuator 262 can be provided to an excitation amplifier circuit 218. The analog signals in the excitation circuit 206 are shown as a fully differential, but such operation is illustratively and one or more portions of the excitation circuit can be single-ended. An output of the excitation amplifier ("D") can be coupled to a switching circuit such as a switch matrix 210 (e.g., where the switches can include solid-state devices such as one or more transistors, or mechanical switching devices). A feedback input of the excitation amplifier 218 can be coupled to the switching matrix, such as to provide flexibility to set excitation amplifier parameters (e.g., gain) using other circuitry connected to the switch matrix 210.

In the illustrative example of FIG. 2, a measurement circuit 208 can include an input amplifier 278 such as including a transimpedance amplifier (TIA). A characteristic of the TIA (e.g., gain) can be established such as using a feedback resistor $R_{tia}$. In an illustrative example, the switch matrix 210, the excitation circuit 206, and the measurement circuit 208 can be co-integrated in a commonly-shared integrated circuit package, and the feedback resistor $R_{tia}$ can be located externally to the commonly-shared integrated circuit package. The input amplifier 278 can be coupled to a variable gain stage 286 and an anti-aliasing filter 288. A digital-to-analog converter (ADC) circuit 290 can convert an input signal to a digital or discrete-time signal. One or more of a gain or offset calibration can be applied at block 292, and a further processing can be performed such as using one or more signal paths selected by a multiplexer 294.

For example, a time-domain windowing function can be applied at block 296 to a series of discrete-time samples and a discrete Fourier transform (DFT) can be performed, such as using hardware-accelerated DFT circuit 212 to provide one or more of real-valued and imaginary-valued outputs. For computational efficiency, the imaginary-valued output 232 can be computed for a single specified frequency or values can be determined a specified range of frequencies. Another signal path can include one or more filters such as a high-frequency rejection filter 298, a decimation block 242, and an optional line frequency rejection filter 244, such as selectable using another multiplexer 246. The measurement circuit 208 signal chain can include a temperature sensing circuit 282 such as providing an output signal selectable by and ADC mux 284.

As an illustrative example, the ADC circuit 290 can provide discrete-time samples having an amplitude resolution of 16 bits (e.g., $2^{16}$ quantizing levels), and the hardware-accelerated DFT circuit 212 can compute a 2048-point single-frequency DFT and provide one or more of real and imaginary-valued components corresponding to a specified frequency.

The switching matrix 210 can be coupled to a biochemical test strip such as through a hardware interface as mentioned in relation to other examples shown and described herein. A calibration device 222, such as a resistor $R_{cal}$ can be connected to terminals 250A and 250B of the switching matrix, such as for use in performing a measurement protocol as described below in relation to FIG. 5. The biochemical test strip assembly can include an identification feature 240, such as can be connected to terminals 250C and 250D.

Figure 3A:
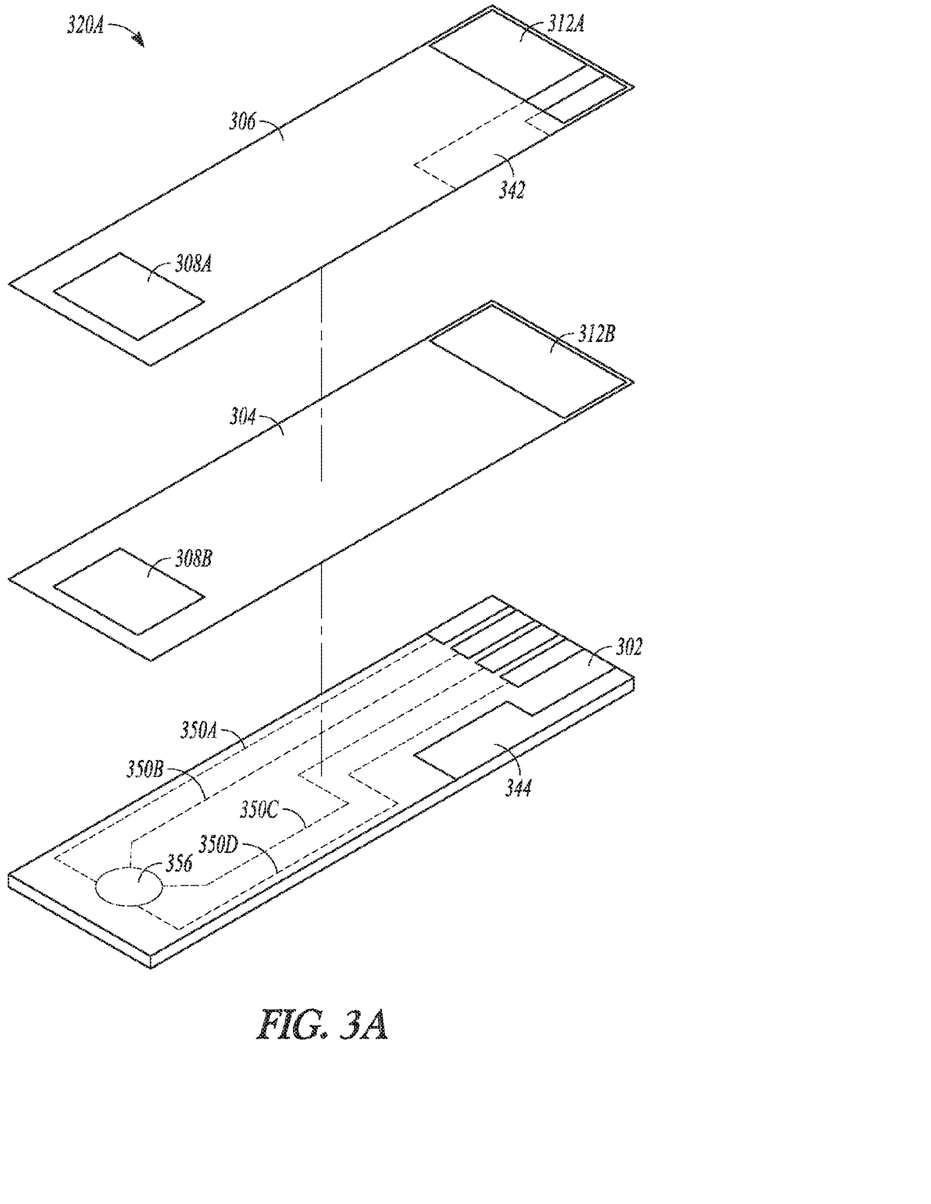
FIGS. 3A and 3B illustrate generally views of an illustrative example of a biochemical test strip assembly, such as can include two or more conductive regions defining an electrical structure that can provide a specified susceptance value for identification of the biochemical test strip assembly.
Figure 3B:
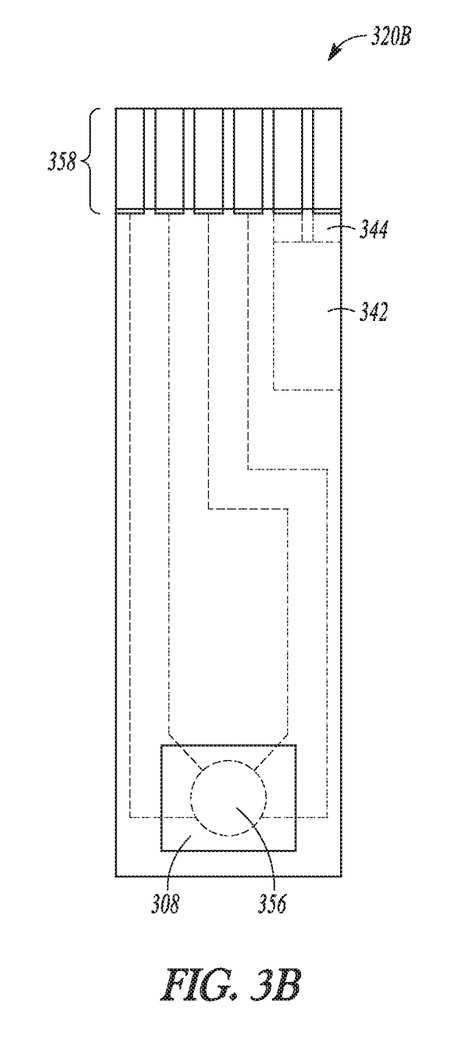

FIGS. 3A and 3B illustrate generally views 320A and 320B of an illustrative example of a biochemical test strip assembly, such as can include two or more conductive regions 342 and 344 defining an electrical structure that can provide a specified susceptance value for identification of the biochemical test strip assembly. In the examples of FIG. 3A and FIG. 3B, a substrate 302 can include a dielectric material such as one or more of an epoxy, a ceramic material such as forming a portion of a low-temperature or high-temperature co-fired ceramic assembly, a glass-epoxy laminate, polyethylene, polypropylene, polystyrene, cellulose, polyethylene terephthalate, or one or more other materials. One or more conductive layers can be formed, such as a conductive layer formed upon a surface of the dielectric material 302, the conductive layer defining the conductive region 344 and one or more other conductive regions such as electrode conductors 350A, 350B, 350C, or 350D. One or more of the electrode conductors 350A, 350B, 350C, or 350D can be arranged to provide electrodes for electrochemical testing such as a reference electrode, a working electrode, or a counter electrode, as illustrative examples. A sample region 356 can include one or more of reagents such as an appropriate enzyme for use in performing an electrochemical measurement for biochemical characterization of a test specimen.

One or more other layers can be used, such as a dielectric separator 304 (e.g., a dielectric film layer). The dielectric separator can conductively isolate a first conductive region 342 of the identification feature from a second conductive region 344 of the identification feature. In another example, the first and second conductive regions 342 and 344 can be formed on different layers (e.g., opposite layers) of a dielectric substrate or film without requiring use of a dielectric separator 304. A dielectric cover layer 306 or mask layer can be included, such as to conductively isolate the first conductive region 342 outside a window 312A. The dielectric separator 304 can include a similar aperture 312B. The conductors 350A, 350B, 350C, and 350D, along with the conductive regions 342 and 344 can be routed to an electrical interface region 358, such as providing exposed contacts (through apertures 312A and 312B) to be probed or coupled to a test circuit such as coupleable to an excitation circuit and a measurement circuit as shown and described above in relation to the examples of FIG. 1 or FIG. 2.

The dielectric separator 304 and the dielectric cover layer 306 can also include respective windows 308A and 308B, such as to provide access to the sample region 356. For example, a drop of blood or another test specimen can be placed upon the sample region 356 in the location 308 as shown in FIG. 3B. A layer including a mesh or screen can be included in the location 308, such as to protect the sample region 356 from mechanical damage or to facilitate wetting or retention of an aqueous sample when applied to the sample region 356. The conductors 350A, 350B, 350C, and 350D shown in FIG. 3A are illustrative and need not all be located on the same conductive layer. For example, some of the conductors could be located in the same layer as the first conductive region 342 or elsewhere.

Figure 3C:
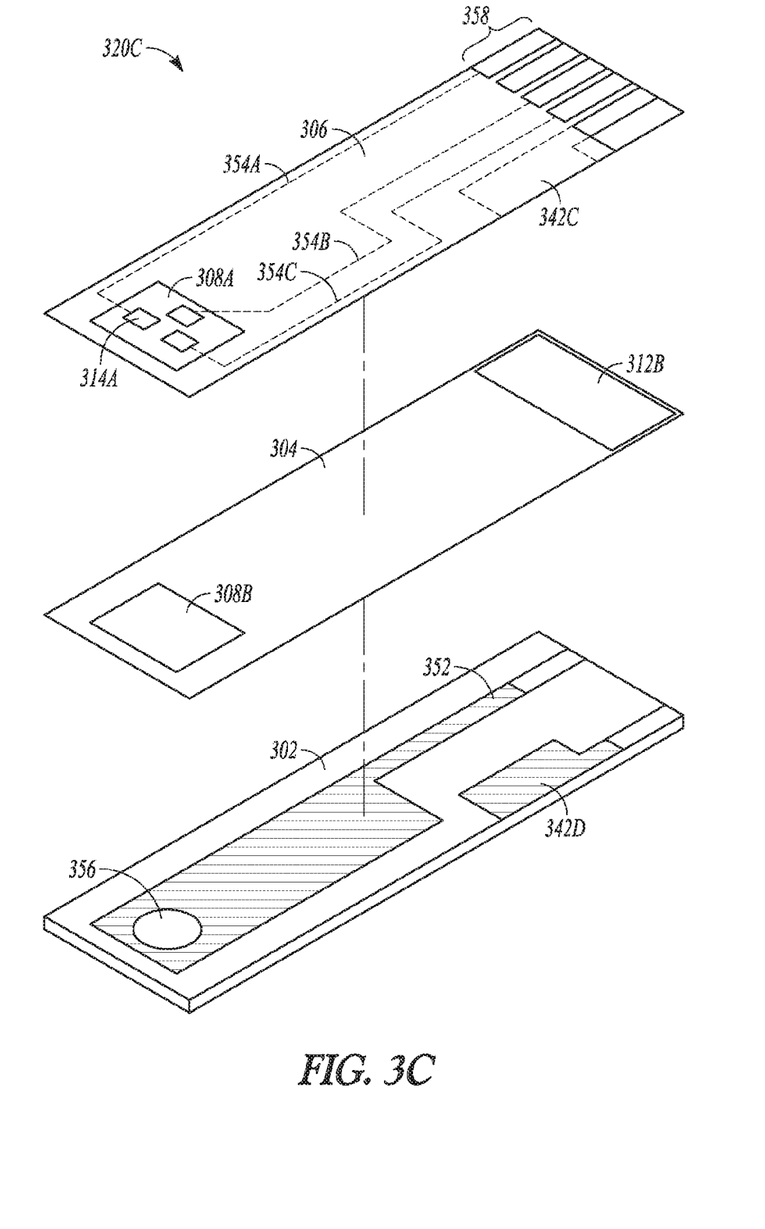
FIG. 3C illustrates generally another illustrative example of a biochemical test strip assembly including another electrical structure that can provide a specified susceptance value for identification of the biochemical test strip assembly.

FIG. 3C illustrates generally another illustrative example of a biochemical test strip assembly 302C including another electrical structure that can provide a specified susceptance value for identification of the biochemical test strip assembly (e.g., an identification feature including a conductive region 342C and a conductive region 342C). In FIG. 3C, a working electrode 352 can be formed such as including a carbon paste material or other conductive material. An enzyme or other reagent can be placed in a sample region 356, and a conductive region 342D of an identification feature 342D can be formed such as using the same material as the working electrode. Contact portions of the working electrode 352 and the conductive region 342D can (but need not) include the same material or can include a layer such as a foil layer to facilitate contact with test circuitry. A dielectric substrate 302 can include one or more materials as mentioned above in relation to the substrate 302 of FIG. 3A or FIG. 3B. Similarly, a dielectric separator 304 can include one or more windows such as a contact window 312B and a sample window 308B. A dielectric cover layer 306 can include a film or thicker substrate. A conductive layer defining one or more electrodes (e.g., an electrode 314A) and conductive traces 354A, 354B, or 354C can provide other electrodes for electrochemical measurement (such as one or more counter electrodes or working electrodes) can be located between the dielectric cover layer 306 and the reference electrode 352 layer. The conductive layer above the dielectric separator 304 can also include another conductive region 342C defining a portion of the identification feature. A susceptance value at a specified frequency can be established by the spatially-overlapping conductive regions 342 and 344 of FIG. 3A or FIG. 3B, or the spatially-overlapping regions 342C and 342D of FIG. 3C, such as shown and described below in relation to FIG. 4. Different test strip assemblies 320A, 320B, or 320C can have identification feature geometries (e.g., size or area, shape, or dimensions) such as to facilitate electrical identification of a test strip. Such identification can be particularized to a single test strip (a unique identification such as a corresponding to a serial number), can provide a lot identification, can provide information traceable to a part or assembly number, or can be used to identify a type of test strip (e.g., to differentiate between test strips configured for different assays, such as a hormonal assay), as illustrative examples.

The conductive materials of the examples of FIG. 3A, FIG. 3B, or FIG. 3C can include one or more of copper, tin, silver, aluminum, palladium, or other materials such as alloys or combinations thereof. Such layers can be formed using one or more of stamping, lithography, screen printing, ink-jet printing, vacuum deposition, or one or more other techniques. In an illustrative example, as shown in FIG. 3C, a conductive layer can include a printed or deposited carbon paste layer.

The conductors in the interface region 358 are shown in FIG. 3A, FIG. 3B, and FIG. 3C as being included as a portion of a conductive layer comprising either the electrochemical test electrodes or one or more portions of the identification feature conductive regions. However, the contacts need not be placed on the same layer as the traces or electrodes used for electrochemical testing. For example, one or more conductive regions can be formed on an exterior surface of the test strip assembly, such as having signals routed using via structures or conductive traces regions bridging one or more conductive layers. The dielectric materials mentioned above including the substrate 302, separator 204, or cover layer 306 can include one or more materials as mentioned above in relation to the substrate 302 or can include one or more other materials. While examples shown in FIG. 3A, FIG. 3B, and FIG. 3C can include laminated or stacked structures, other configurations can be used, such as an encapsulated structure or an over-molded structure wherein one or more conductive regions are encapsulated or over-molded with one or more dielectric materials. In an example, one or more dielectric structures can include an adhesive or an adhesive layer such as a pressure-sensitive adhesive, to bind the layers together. In another example, a b-staged epoxy can be used (such as a pre-preg), and cured laminated structure can be formed such as by treating the assembly with heat.

Figure 4:
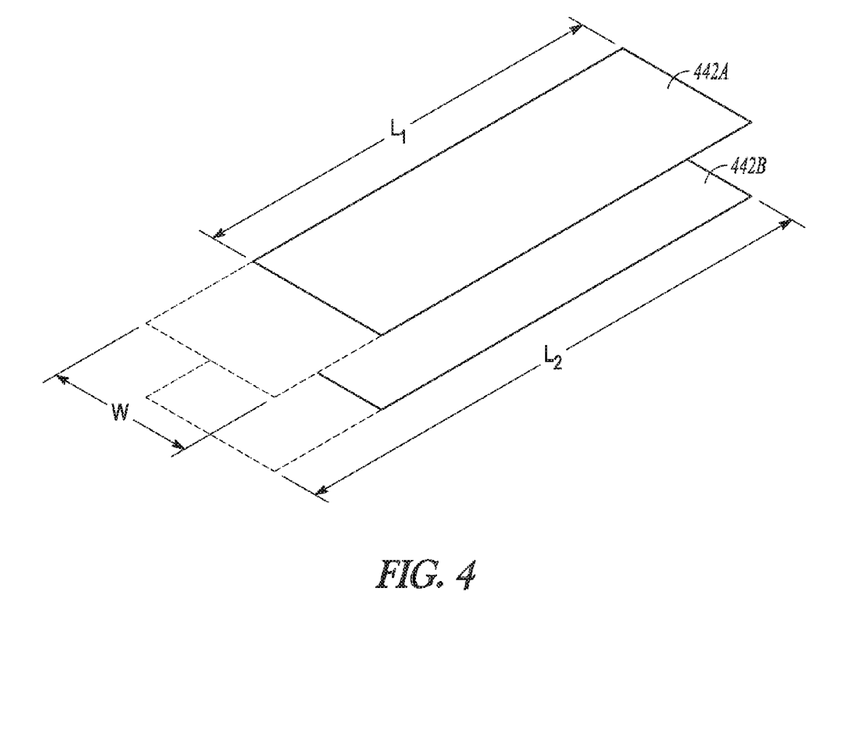
FIG. 4 illustrates generally an arrangement of conductive regions having one or more geometric or spatial characteristics that can be adjusted to provide a specified susceptance value for identification of the biochemical test strip assembly.

FIG. 4 illustrates generally an arrangement of conductive regions having one or more geometric or spatial characteristics that can be adjusted to provide a specified susceptance value for identification of the biochemical test strip assembly. For example, a first conductive region 442A can be rectangular, such as having a length, $L_1$, and a width, W. The second conductive region 442B can have a similar length and width, or can have one or more of a different length or width. The degree of overlap between the first and second conductive regions 442A and 442B can be varied, such as by offsetting the first conductive region 442A laterally from the second conductive region 442B, or by adjusting a length or width of one or both of the conductive regions as shown (such as to provide a different length, $L_2$, as an illustrative example, or a different width). A height or vertical separation between the first and second conductive regions 442A and 442B can also be used to set the specified susceptance of the identification feature.

The example of FIG. 4 shows a rectangular or rectilinear shape, but other shapes can be used, such as to avoid interfering electrically or mechanically with other features on a biochemical test strip. A susceptance value of the conductors 442A and 442B of the structure shown in FIG. 4 can be used to identify a test strip, such as mentioned above, by lot, type, expiration, or one or more other values. Details correlating susceptance values to particular identification information can be stored on an interrogation device, such as permanently stored or updated at specified intervals using information obtained from elsewhere such as from a user or centralized database. An array of conductive regions can be provided, such as to provide binary or decimal encoding of identification information to provide additional degrees of freedom beyond using a scalar susceptance value.

Figure 5:
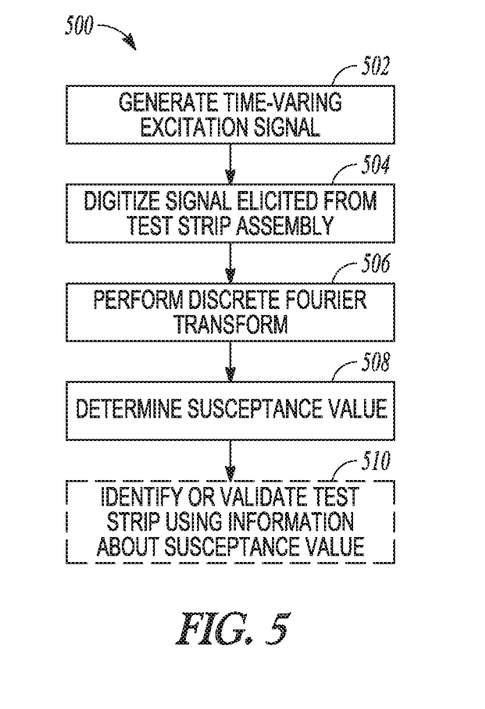
FIG. 5 illustrates generally a technique, such as a method, that can include generating a time-varying excitation signal to probe an electrical structure included as a portion of a biochemical test strip assembly, and determining a susceptance value that can be used to identify or validate the biochemical test strip assembly.

FIG. 5 illustrates generally a technique 500, such as a method, that can include at 502 generating a time-varying excitation signal such as to probe an electrical structure included as a portion of a biochemical test strip assembly. At 504, a signal elicited from the test strip assembly can be digitized. As discussed below, the time-varying excitation signal can include a specified current, and the elicited signal can include a detected voltage (force-I/measure-V or FIMV), or the time-varying excitation signal can include a specified voltage, and the elicited signal can include a detected current (force-V/measure-I or FVMI). At 506, a discrete Fourier transform can be performed on a discrete-time representation of the elicited signal digitized at 504, and at 508 a susceptance value can be determined. At 510, information indicative of the susceptance value can be used such as to identify a biochemical test strip or to validate a test strip for use, such as prior to obtaining electrochemical measurement or prior to presenting results of an electrochemical measurement to a user. The technique 500 can be performed such as using a mains-powered or battery operated interrogation device, such as a table-top or hand-held testing device having a hardware interface to receive and electrically couple a biochemical test strip to other circuitry comprising the interrogation device. For example, a biochemical test strip can include a rectangular assembly insertable into a slot or receptacle included as a portion of the interrogation device.

Generally, admittance, Y, can be defined as the inverse of an impedance, $Y=1/Z$, and the admittance can be complex-valued (a vector quantity), having a real-valued component, G, providing a conductance contribution, and an imaginary-valued component, B, providing a susceptance value where $Y=G+jB$, where "j" represents $\sqrt{-1}$. Various approaches can be used to perform a susceptance measurement, such as using a calibration technique.

In one approach, a fixed alternating current (AC) voltage magnitude can be applied across a calibration resistor having a known value (e.g., RCAL), such as including also applying a known common mode voltage across the terminals of the calibration resistor. A relative change in current can be measured (e.g., digitized) and a discrete Fourier transform (DFT) can be performed on the measured current obtain real-valued and imaginary-valued components of the calibration current measurement. The values of the conductance and susceptance can be determined such as by dividing the measured real-valued and imaginary-valued components by the voltage magnitude.

The fixed AC voltage can be applied across the terminals of the identification feature (e.g., with one terminal connected to a first conductive region, and a second terminal connected to a second conductive region), and a known common-mode voltage can also be applied across the terminals. A relative change in current can be measured and the DFT can be performed to obtain real-valued and imaginary-valued components of the identification feature current measurement. A complex-valued subtraction can be performed, such as by subtracting the susceptance value obtained by measuring the identification feature from the susceptance value of the calibration measurement to obtain a corrected or calibrated susceptance value corresponding to the identification feature. The corrected or calibrated susceptance value can then be provided for use in identification of the test strip.

In another approach, a fixed AC current magnitude can be forced through the calibration device and a differential voltage can be measured across the calibration device. Similarly, the fixed AC current magnitude can be forced through the identification feature (from a first conductive region to a second conductive region), and a differential voltage can be measured across the identification feature. A determined susceptance value of the identification feature can be corrected such as by subtracting a measured susceptance value obtained for the calibration device.

VARIOUS NOTES & EXAMPLES

Example 1 can include or use subject matter (such as an apparatus, a method, a means for performing acts, or a device readable medium including instructions that, when performed by the device, can cause the device to perform acts), such as can include or use an electronic system comprising an excitation source configured to generate a time-varying excitation signal to be conductively coupled to a biochemical test strip assembly, a measurement circuit comprising an analog-to-digital converter, the measurement circuit configured to digitize a signal elicited from the biochemical test strip assembly by the excitation signal, perform a discrete Fourier transform on the digitized signal and determine a susceptance value from the digitized signal to identify the biochemical test strip, where the biochemical test strip assembly includes two or more conductive regions configured to establish a specified susceptance value within a specified range when measured at a specified frequency, for measurement by the measurement circuit, the susceptance value established to permit identification the biochemical test strip assembly.

In Example 2, the subject matter of Example 1 optionally includes that the biochemical test strip assembly includes at least two measurement electrodes conductively coupled to a sample region, an identification feature including a first conductive region defining a first portion of an electrical structure and a second conductive region, conductively isolated from the first conductive region, defining a second portion of the electrical structure, and an interface region defining an electrical interface electrically connecting the at least two measurement electrodes and the identification feature of the biochemical test strip assembly to an interrogation device comprising the excitation source and the measurement circuit, where the first and second conductive regions are sized and shaped to provide the specified susceptance value within the specified range when measured at the specified frequency.

In Example 3, the subject matter of any one or more of Examples 1 through 2 optionally include a switching circuit configured to selectively couple the excitation source and measurement circuit to specified conductive regions of the biochemical test strip to (a) identify the biochemical test strip using a measurement susceptance value and (b) to perform excitation and measurement operations for electrochemical measurement using a sample region and electrodes included as a portion of the biochemical test strip.

In Example 4, the subject matter of any one or more of Examples 1 through 3 to optionally include a calibration device coupleable to the excitation source and the measurement circuit.

In Example 5, the subject matter of any one or more of Examples 1 through 4 optionally include a hardware-accelerated discrete Fourier transform (DFT) circuit, where the measurement circuit is configured to perform the discrete Fourier transform of the digitized signal using the hardware-accelerated DFT circuit.

In Example 6, the subject matter of Example 5 optionally includes that the hardware-accelerated DFT circuit is configured to perform a single-frequency DFT.

In Example 7, the subject matter of any one or more of Examples 1 through 6 optionally includes a processor circuit coupled to the measurement circuit, the processor circuit configured to select an electrochemical measurement protocol in response to identification of the biochemical test strip, the identification performed at least in part using the determined susceptance value.

In Example 8, the subject matter of any one or more of Examples 1 through 7 optionally include a hardware sequencer circuit configured to control the excitation source and the measurement circuit.

Example 9 can include, or can optionally be combined with the subject matter of one or any combination of Examples 1 through 8 to include, subject matter (such as an apparatus, a method, a means for performing acts, or a machine readable medium including instructions that, when performed by the machine, that can cause the machine to perform acts), such as can include identifying a biochemical test strip assembly, including generating a time-varying excitation signal and conductively coupling the generated time-varying excitation signal to a biochemical test strip assembly, digitizing a signal elicited from the biochemical test strip assembly by the excitation signal, using a circuit, performing a discrete Fourier transform on the digitized signal, and using an output of the discrete Fourier transform, determining a susceptance value from the digitized signal to identify the biochemical test strip, where the biochemical test strip assembly includes two or more conductive regions configured to establish a specified susceptance value within a specified range when measured at a specified frequency, the susceptance value established to permit identification the biochemical test strip assembly.

In Example 10, the subject matter of Example 9 optionally includes performing excitation and measurement operations for electrochemical measurement according to a specified electrochemical measurement protocol under the control of a processor circuit, using a sample region and electrodes included as a portion of the biochemical test strip.

In Example 11, the subject matter of any one or more of Examples 9 or 10 optionally includes, using a processor circuit, selecting an electrochemical measurement protocol in response to identification of the biochemical test strip, the identification performed automatically at least in part using the determined susceptance value.

In Example 12, the subject matter of any one or more of Examples 9 through 11 optionally includes establishing a specified common-mode voltage across a calibration device, forcing a specified time-varying voltage signal across the calibration device, digitizing a relative change in current through the calibration device to provide a digitized calibration signal, performing a discrete Fourier Transform (DFT) on the digitized calibration signal to generate an imaginary-valued component of the digitized calibration signal, establishing a specified common-mode voltage across an identification feature of a biochemical test strip, the identification feature comprising first and second conductive regions conductively isolated from each other, forcing a specified time-varying voltage signal across the identification feature, digitizing a relative change in current through the identification feature to provide a digitized identification signal, performing a discrete Fourier Transform (DFT) on the digitized identification signal to generate an imaginary-valued component of the digitized identification signal, and adjusting the imaginary-valued component of the digitized identification signal using the imaginary-valued component of the digitized calibration signal to provide the susceptance value.

In Example 13, the subject matter of any one or more of Examples 9-12 optionally include forcing a specified time-varying current through a calibration device; digitizing a differential voltage across the calibration device to provide a digitized calibration signal; performing a discrete Fourier Transform (DFT) on the digitized calibration signal to generate an imaginary-valued component of the digitized calibration signal; forcing a specified time-varying current through an identification feature of a biochemical test strip, the identification feature comprising first and second conductive regions conductively isolated from each other; digitizing a differential voltage across the identification feature to provide a digitized identification signal; performing a discrete Fourier Transform (DFT) on the digitized identification signal to generate an imaginary-valued component of the digitized identification signal; and adjusting the imaginary-valued component of the digitized identification signal using the imaginary-valued component of the digitized calibration signal to provide the susceptance value.

In Example 14, the subject matter of any one or more of Examples 9 through 13 optionally include selectively coupling one or more of a source of the time-varying excitation signal, or a digitizer to perform the digitizing, to specified electrodes included as a portion of the biochemical test strip using a switching circuit.

Example 15 can include, or can optionally be combined with the subject matter of one or any combination of Examples 1 through 14 to include, subject matter (such as an apparatus, a method, a means for performing acts, or a machine readable medium including instructions that, when performed by the machine, that can cause the machine to perform acts), such as can include a biochemical test strip assembly, comprising at least two measurement electrodes conductively coupled to a sample region; an identification feature including a first conductive region defining a first portion of an electrical structure and a second conductive region, conductively isolated from the first conductive region, defining a second portion of the electrical structure; and an interface region comprising conductive portions forming an electrical interface electrically connecting the at least two measurement electrodes and the identification feature of the biochemical test strip assembly to an interrogation device; wherein the first and second conductive regions are sized and shaped to provide a specified susceptance value within a specified range when measured at a specified frequency, the susceptance value established to permit identification the biochemical test strip assembly.

In Example 16, the subject matter of Example 15 optionally includes a dielectric layer, where the first conductive region is located on a first conductive layer on first surface of the dielectric layer and where the second conductive region is located on a second conductive layer on a second surface of the dielectric layer opposite the first surface.

In Example 17, the subject matter of Example 16 optionally includes wherein the first and second conductive regions have a specified area of overlap to establish the susceptance value.

In Example 18, the subject matter of Example 17 optionally includes that the first and second conductive regions include rectangular portions having a specified length and width to establish the susceptance value.

In Example 19, the subject matter of any one or more of Examples 15 through 18 optionally include a dielectric substrate, a first conductive layer defining the measurement electrodes and the first conductive region, a dielectric separator, a second conductive layer defining the second conductive region, the second conductive region isolated from the first conductive region using the dielectric separator.

In Example 20, the subject matter of any one or more of Examples 15 through 19 optionally include that the two or more measurement electrodes and the first and second conductive regions are conductively coupled to an electrical interconnect comprising a portion of the biochemical test strip assembly.

Example 21 can include, or can optionally be combined with any portion or combination of any portions of any one or more of Examples 1 through 20 to include, subject matter that can include means for performing any one or more of the functions of Examples 1 through 20, or a machine-readable medium including instructions that, when performed by a machine, cause the machine to perform any one or more of the functions of Examples 1 through 20. Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An electronic system, comprising:
   an excitation source configured to generate a time-varying excitation signal to be conductively coupled to a biochemical test strip assembly, and configured to apply a specified time-varying signal to a calibration device;
   a measurement circuit comprising an analog-to-digital converter, the measurement circuit configured to digitize a calibration signal from the calibration device, the calibration signal elicited by the applied specified time-varying signal, and to digitize an identification signal elicited from the biochemical test strip assembly by the excitation signal, perform a discrete Fourier transform on the digitized identification signal, and determine a susceptance value from the digitized identification signal to identify the biochemical test strip, including adjusting an imaginary-valued component of the digitized identification signal using an imaginary-valued component of the digitized calibration signal;
   wherein the biochemical test strip assembly includes two or more conductive regions configured to establish a specified susceptance value within a specified range when measured at a specified frequency, for measurement by the measurement circuit, the susceptance value established to permit identification the biochemical test strip assembly.

2. The electronic system of claim 1, further comprising the biochemical test strip assembly, the assembly including:
   at least two measurement electrodes conductively coupled to a sample region;
   an identification feature including:
   a first conductive region amongst the two or more conductive regions, defining a first portion of an electrical structure; and
   a second conductive region amongst the two or more conductive regions, conductively isolated from the first conductive region, defining a second portion of the electrical structure; and
   an interface region defining an electrical interface electrically connecting the at least two measurement electrodes and the identification feature of the biochemical test strip assembly to an interrogation device comprising the excitation source and the measurement circuit;
   wherein the first and second conductive regions are sized and shaped to provide the specified susceptance value within the specified range when measured at the specified frequency.

3. The electronic system of claim 1, comprising a switching circuit configured to selectively couple the excitation source and measurement circuit to specified conductive regions amongst the two or more conductive regions, of the biochemical test strip assembly to (a) identify the biochemical test strip assembly using a measurement susceptance value and (b) to perform excitation and measurement operations for electrochemical measurement using a sample region and electrodes included as a portion of the biochemical test strip.

4. The electronic system of claim 3, comprising the calibration device coupleable to the excitation source and the measurement circuit.

5. The electronic system of claim 1, comprising a hardware-accelerated discrete Fourier transform (DFT) circuit; and
wherein the measurement circuit is configured to perform the discrete Fourier transform of the digitized identification signal using the hardware-accelerated DFT circuit.

6. The electronic system of claim 5, wherein the hardware-accelerated DFT circuit is configured to perform a single-frequency DFT.

7. The electronic system of claim 1, comprising a processor circuit coupled to the measurement circuit, the processor circuit configured to select an electrochemical measurement protocol in response to identification of the biochemical test strip, the identification performed at least in part using the determined susceptance value.

8. The electronic system of claim 1, comprising a hardware sequencer circuit configured to control the excitation source and the measurement circuit.

9. The electronic system of claim 2, comprising a dielectric layer;
wherein the first conductive region is located on a first conductive layer on first surface of the dielectric layer; and
wherein the second conductive region is located on a second conductive layer on a second surface of the dielectric layer opposite the first surface.

10. The electronic system of claim 9, wherein the first and second conductive regions have a specified area of overlap to establish the susceptance value.

11. The electronic system of claim 10, wherein the first and second conductive regions include rectangular portions having a specified length and width to establish the susceptance value.

12. The electronic system of claim 2, comprising:
a dielectric substrate;
a first conductive layer defining the measurement electrodes and the first conductive region;
a dielectric separator;
a second conductive layer defining the second conductive region, the second conductive region isolated from the first conductive region using the dielectric separator.

13. The electronic system of claim wherein the two or more measurement electrodes and the first and second conductive regions are conductively coupled to an electrical interconnect comprising a portion of the biochemical test strip assembly.

14. A method for identifying a biochemical test strip assembly; the method comprising:
applying a specified time-varying signal to a calibration device;
digitizing a calibration signal from the calibration device, the calibration signal elicited by the applied specified time-varying signal;
generating a time-varying excitation signal and conductively coupling the generated time-varying excitation signal to a biochemical test strip assembly;
digitizing an identification signal elicited from the biochemical test strip assembly by the excitation signal;
using a circuit; performing a discrete Fourier transform on the digitized identification signal; and
using an output of the discrete Fourier transform, determining a susceptance value from the digitized identification signal to identify the biochemical test strip, including adjusting an imaginary-valued component of the digitized identification signal using an imaginary-valued component of the digitized calibration signal;
wherein the biochemical test strip assembly includes two or more conductive regions configured to establish a specified susceptance value within a specified range when measured at a specified frequency, the susceptance value established to permit identification the biochemical test strip assembly.

15. The method of claim 14, comprising performing excitation and measurement operations for electrochemical measurement according to a specified electrochemical measurement protocol under the control of a processor circuit, using a sample region and electrodes included as a portion of the biochemical test strip.

16. The method of claim 14, comprising, using a processor circuit, selecting an electrochemical measurement protocol in response to identification of the biochemical test strip, the identification performed automatically at least in part using the determined susceptance value.

17. The method of claim 14, comprising:
establishing a specified common-mode voltage across the calibration device;
forcing a specified time-varying voltage signal across the calibration device;
digitizing a relative change in current through the calibration device to provide the digitized calibration signal;
performing a discrete Fourier Transform (DFT) on the digitized calibration signal to generate the imaginary-valued component of the digitized calibration signal;
establishing a specified common-mode voltage across an identification feature of the biochemical test strip assembly, the identification feature comprising first and second conductive regions amongst the two or more conductive regions, conductively isolated from each other;
forcing a specified time-varying voltage signal across the identification feature;
digitizing a relative change in current through the identification feature to provide the digitized identification signal;
performing a discrete Fourier Transform (DFT) on the digitized identification signal to generate the imaginary-valued component of the digitized identification signal; and
adjusting the imaginary-valued component of the digitized identification signal using the imaginary-valued component of the digitized calibration signal to provide the susceptance value.

18. The method of claim 14, comprising:
forcing a specified time-varying current through the calibration device;
digitizing a differential voltage across the calibration device to provide the digitized calibration signal;
performing a discrete Fourier Transform (DFT) on the digitized calibration signal to generate the imaginary-valued component of the digitized calibration signal;
forcing a specified time-varying current through an identification feature of the biochemical test strip assembly, the identification feature comprising first and second conductive regions amongst the two or more conductive regions, conductively isolated from each other;
digitizing a differential voltage across the identification feature to provide the digitized identification signal;
performing a discrete Fourier Transform (DFT) on the digitized identification signal to generate the imaginary-valued component of the digitized identification signal; and adjusting the imaginary-valued component of the digitized identification signal using the imaginary-valued component of the digitized calibration signal to provide the susceptance value.

19. The method of claim 14, comprising selectively coupling one or more of a source of the time-varying excitation signal, or a digitizer to perform the digitizing, to specified electrodes included as a portion of the biochemical test strip using a switching circuit.

20. An electronic system for identifying a biochemical test strip assembly, the electronic system comprising:
    a signal source means for applying a specified time-varying signal to a calibration device;
    a means for digitizing a calibration signal from the calibration device, the calibration signal elicited by the applied specified time-varying signal;
    a means for generating a time-varying excitation signal and conductively coupling the generated time-varying excitation signal to the biochemical test strip assembly;
    a means for digitizing an identification signal elicited from the biochemical test strip assembly by the excitation signal;
    a means for performing a discrete Fourier transform on the digitized identification signal; and
    using an output of the discrete Fourier transform, a means for determining a susceptance value from the digitized identification signal to identify the biochemical test strip including adjusting an imaginary-valued component of the digitized identification signal using an imaginary-valued component of the digitized calibration signal;
    wherein the biochemical test strip assembly includes an identification feature to establish a specified susceptance value within a specified range when measured at a specified frequency, the susceptance value established to permit identification the biochemical test strip assembly.

21. The electronic system of claim 20, comprising performing excitation and measurement operations for electrochemical measurement according to a specified electrochemical measurement protocol under the control of a processing means, using a sample region and electrodes included as a portion of the biochemical test strip.

22. The electronic system of claim 20, comprising, using the processing means, selecting an electrochemical measurement protocol in response to identification of the biochemical test strip, the identification performed automatically at least in part using the determined susceptance value.

* * * * *

UNITED STATES PATENT AND TRADEMARK OFFICE
CERTIFICATE OF CORRECTION

PATENT NO. : 10,386,324 B2  
APPLICATION NO. : 15/050141  
DATED : August 20, 2019  
INVENTOR(S) : Riordan et al.

Page 1 of 1

It is certified that error appears in the above-identified patent and that said Letters Patent is hereby corrected as shown below:

In the Claims

In Column 15, Line 43, in Claim 13, after "claim", insert --2,--

In Column 15, Line 49, in Claim 14, delete "assembly;" and insert --assembly,-- therefor In Column 15, Line 60, in Claim 14, delete "circuit;" and insert --circuit,-- therefor In Column 15, Line 64, in Claim 14, delete "strip," and insert --strip-- therefor Signed and Sealed this  
Third Day of March, 2020

Andrei Iancu  
*Director of the United States Patent and Trademark Office*